United States Patent [19]

Richardson et al.

[11] Patent Number: 4,483,863

[45] Date of Patent: Nov. 20, 1984

[54] TRIAZOLE ANTIFUNGAL AGENTS

[75] Inventors: Kenneth Richardson; Geoffrey Gymer, both of Canterbury, England

[73] Assignee: Pfizer Inc., New York, N.Y.

[21] Appl. No.: 572,332

[22] Filed: Jan. 20, 1984

[51] Int. Cl.³ .................... A01N 43/64; A61K 31/41; C07D 249/08; C07D 403/06

[52] U.S. Cl. .................................. 424/269; 548/101; 548/252; 548/262; 548/269

[58] Field of Search ....................... 548/252, 262, 269; 424/269

[56] References Cited

U.S. PATENT DOCUMENTS 4,416,682 11/1983 Worthington ...................... 548/262

FOREIGN PATENT DOCUMENTS 0044605 1/1982 European Pat. Off. ............ 548/262
2099818 12/1982 United Kingdom ................ 548/262

Primary Examiner—Alton D. Rollins
Attorney, Agent, or Firm—Charles J. Knuth; Albert E. Frost; James M. McManus

[57] ABSTRACT

Compounds of the general formula:

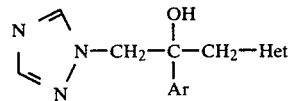

wherein Ar is dichlorophenyl and Het is 1-methyltetrazol-5-yl, 1,2,4-triazol-3-yl, 1-methyl-1,2,4-triazol-3-yl, 2-methyl-1,2,4-triazol-3-yl, 4-methyl-1,2,4-triazol-3-yl, imidazol-2-yl or 1-methylimidazol-2-yl and their pharmaceutically acceptable acid addition salts are antifungal agents in humans and other animals.

5 Claims, No Drawings

TRIAZOLE ANTIFUNGAL AGENTS

BACKGROUND OF THE INVENTION

This invention relates to novel triazole derivatives which have antifungal activity and are useful in the treatment of fungal infections in animals, including humans.

British Patent Application No. 2078719A and European Patent Application No. 44605 disclose certain 1,3-bis-heterocyclyl-2-aryl-propan-2-ol derivatives wherein the heterocyclic group is a (1,2,4-triazol-1-yl) or (imidazol-1-yl) group. The compounds are stated to be useful as plant fungicides and growth regulators and also for the treatment of fungal diseases in humans and other animals.

SUMMARY OF THE INVENTION

The compounds of the present invention are of the formula

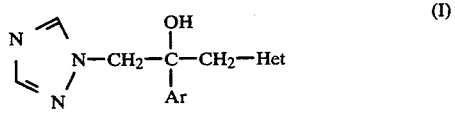

(I)

and the pharmaceutically acceptable acid addition salts thereof, where Ar is dichlorophenyl and Het is 1-methyltetrazol-5-yl, 1,2,4-triazol-3-yl, 1-methyl-1,2,4-triazol-3-yl, 2-methyl-1,2,4-triazol-3-yl, 4-methyl-1,2,4-triazol-3-yl, imidazol-2-yl or 1-methylimidazol-2-yl.

A preferred group of compounds are those wherein Ar is 2,4-dichlorophenyl; especially preferred is 2-(2,4-dichlorophenyl)-1-(1-methyltetrazol-5-yl)-3-(1H,1,2,4-triazol-1-yl)propan-2-ol.

The invention also providees a pharmaceutical composition comprising a compound of formula (I) or a pharmaceutically acceptable acid addition salt thereof, together with a pharmaceutically acceptable diluent or carrier.

The invention further provides a compound of the formula (I) or a pharmaceutically acceptable acid addition salt thereof, for use in medicine, in particular for use in treating a fungal infection in a human being.

DETAILED DESCRIPTION OF THE INVENTION

The compounds of formula (I) wherein Het is 1-methyltetrazolyl can be prepared according to the following reaction scheme wherein Ar is as previously defined.

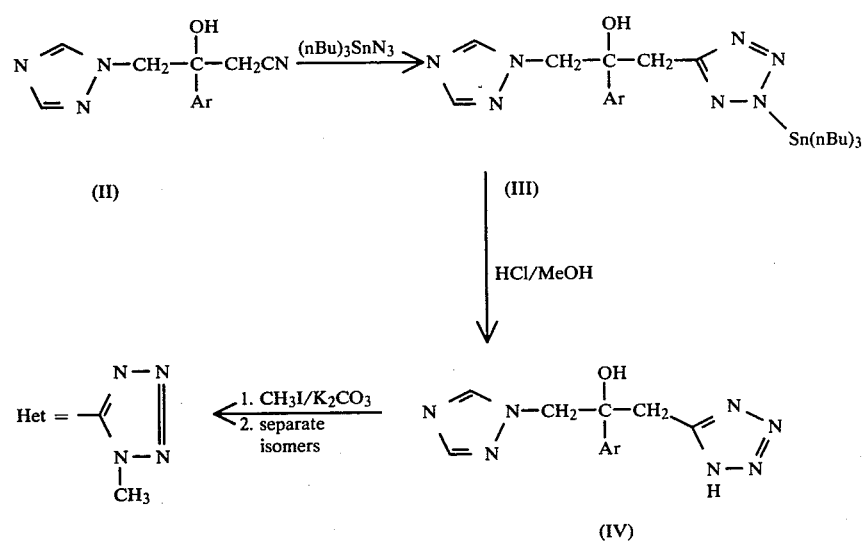

The reaction between the nitrile (II) and tri-n-butyltin azide is simply performed by heating the reactants together. A 10–20% molar excess of the azide is preferably used to ensure complete reaction. A temperature in the range of 100° to 180° C. can be used. The period required for completion of the reaction will depend upon the precise nature of the reactants and the temperature employed; generally a period of three hours at 160° C. is sufficient. The reaction mixture is cooled and triturated with an organic solvent to remove unreacted azide and provide the product (III). This is decomposed by suspending in a solution of methanolic hydrogen chloride at room temperature for several hours to provide the tetrazole derivative (IV).

The final methylation step is performed in a conventional manner by treating the tetrazole (IV) with methyl iodide and potassium carbonate in an inert organic solvent, e.g. N,N-dimethylformamide. A period of three hours at room temperature is generally sufficient to ensure complete reaction and the resulting mixture of the 1-methyl and 2-methyl-tetrazole isomers is separated by chromatography to yield the desired product.

The compounds of the formula (I) wherein Het is triazolyl or 1-, 2-, 4-methyltriazolyl may be prepared according to the following reaction scheme wherein Ar is as previously defined:

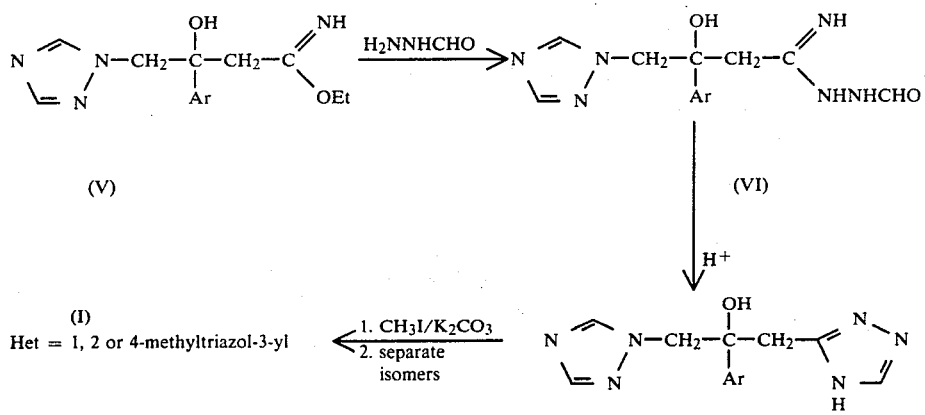

(V)

(VI)

(I)
Het = 1, 2 or 4-methyltriazol-3-yl

The reaction between the imino ether (V) and formyl hydrazine is performed by adding the reactants in equimolar proportions to an inert organic solvent, for example methylene chloride; a period of 12 hours at room temperature is generally sufficient to enable the reaction to go to completion. The intermediate (VI) need not be isolated, but is heated in an inert organic solvent, e.g. toluene in the presence of a trace of acid, e.g. para-toluenesulphonic acid, to effect ring closure, providing the derivative of formula (I) wherein Het is 1,2,4-triazol-3-yl. The product is isolated in a conventional manner by washing and evaporation of the solvent. The crude product may be further purified, if required, by chromatography or by salt formation.

Compounds wherein Het is 1-, 2- or 4-methyl-triazolyl are readily prepared by methylation of the unsubstituted triazolyl derivative using a conventional methylation reaction, for example using methyl iodide and potassium carbonate, as already described for the tetrazole derivative. In this case the product is obtained as a mixture of the three possible N-methyl isomers and are separated by chromatography to yield the desired 1-, 2-, and 4-methyl isomers.

The compounds of the formula (I) wherein Het is 2-imidazolyl may be prepared from the imino ether (V) by first reacting with aminoacetaldehyde as its diethyl acetal followed by treatment with acid to effect ring closure. The 1-methylimidazolyl derivative is again readily prepared by methylation of the unsubstituted compound, for example by reacting with methyliodide and potassium carbonate in acetone.

Pharmaceutically acceptable acid addition salts of the compounds of the formula (I) are those formed from strong acids which form non-toxic acid addition salts, such as hydrochloric, hydrobromic, sulphuric, oxalic and methanesulphonic acids.

The salts may be obtained by conventional procedures, e.g. by mixing solutions containing approximately equimolar amounts of the free base and desired acid, and the required salt is collected by filtration, if insoluble, or by evaporation of the solvent.

The compounds of the formula (I) and their pharmaceutically acceptable salts are antifungal agents, useful in combating fungal infections in animals, including humans. For example they are useful in treating topical fungal infections in man caused by, among other organisms, species of Candida, Trichophyton, Microsporum, or Epidermophyton, or in mucosal infections caused by *Candida albicans* (e.g. thrush and vaginal candidiasis). They can also be used in the treatment of systemic fungal infections caused by, for example, *Candida albicans, Cryptococcus neoformans, Aspergillus fumigatus,* Coccidioides, Paracoccidioides, Histoplasma or Blastomyces.

The in vitro evaluation of the antifungal activity of the compounds can be performed by determining the minimum inhibitory concentration (m.i.c.) of the test compounds in a suitable medium at which growth of the particular microorganism fails to occur. In practice, a series of agar plates, each having the test compound incorporated at a particular concentration is inoculated with a standard culture of, for example, *Candida albicans* and each plate is then incubated for 48 hours at 37° C. The plates are then examined for the presence or absence of growth of the fungus and the appropriate m.i.c. value is noted. Other microorganisms used in such tests can include *Cryptococcus neoformans, Aspergillus fumigatus,* Trichophyton spp; Microsporum spp; *Epidermophyton floccosum, Coccidioides immitis* and *Torulopsis glabrata*.

The in vivo evaluation of the compounds can be carried out at a series of dose levels by intraperitoneal or intravenous injection or by oral administration, to mice which are inoculated with a strain of *Candida albicans*. Activity is based on the survival of a treated group of mice after the death of an untreated group of mice following 48 hours observation. The dose level at which the compound provides 50% protection against the lethal effect of the infection is noted.

For human use, the antifungal compounds of the formula (I) can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs or suspensions containing flavouring colouring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For oral and parenteral administration to human patients, the daily dosage level of the antifungal compounds of the formula (I) will be from 0.1 to 10 mg/kg (in divided doses) when administered by either the oral or parenteral route. Thus tablets or capsules of the compounds will contain from 5 mg to 0.5 g of active compound for administration singly or two or more at a time as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited, and such are within the scope of this invention.

Alternatively, the antifungal compounds of formula (I) can be administered in the form of a suppository or pessary, or they may be applied topically in the form of a lotion, solution, cream, ointment or dusting powder. For example, they can be incorporated into a cream consisting of an aqueous emulsion of polyethylene glycols or liquid paraffin; or they can be incorporated, at a concentration between 1 and 10%, into an ointment consisting of a white wax or white soft paraffin base together with such stabilizers and preservatives as may be required.

The compounds of the formula (I) and their salts also have activity against a variety of plant pahogenic fungi, including for example various rusts, mildews and moulds, and the compounds are thus useful as agricultural fungicides for treating plants and seeds to eradicate or prevent such diseases.

The following Examples illustrate the invention.

EXAMPLE 1

2-(2,4-Dichlorophenyl)-1-(1-methyltetrazol-5-yl)-3-(1H-1,2,4-triazol-1-yl)propan-2-ol 1. A paste of tri-n-butyltin azide (2.45 g) and 1-cyano-2-(2,4-dichlorophenyl)-3-(1H-1,2,4-triazol-1-yl)propan-2-ol (2.0 g) was heated at 160° C. for three hours. A further quantity of tri-n-butyltin azide (0.2 g) was added and the heating continued for a further hour to complete the reaction. The resulting viscous oil was triturated with ethyl acetate and the product collected and dried under vacuum to give 2-(2,4-dichlorophenyl)-1-(1H-1,2,4-triazol-1-yl)-3-(2-tribut-1-ylstannyltetrazol-5-yl)propan-2-ol as a crystalline solid (3.1 g, 73%) m/e 628.

2. The product from the first stage was suspended in methanol (100 ml) and a rapid stream of hydrogen chloride gas was passed through the solution for ten minutes. The solution was then stirred for three hours and the solvent was evaporated under reduced pressure. The residue was triturated with several portions of diisopropyl ether and the resulting white solid was crystallized from water to give 2-(2,4-dichlorophenyl)-1-(tetrazol-5-yl)-3-(1H-1,2,4-triazol-1-yl)propan-2-ol (1.6 g, 95%), m.p. 214°-215° C. Found: C,42.4; H,3.4; N,27.7. $C_{12}H_{11}Cl_2N_7O$ requires C,42.3; H,3.3; N,28.8%.

3. A solution of the tetrazole product from the second stage (1.3 g) in N,N-dimethylformamide (25 ml) was stirred with methyl iodide (2.5 g) and excess potassium carbonate (1.3 g) at room temperature for three hours. The reaction mixture was then diluted with water (75 ml) and extracted with ethyl acetate (3×50 ml). The combined extracts were washed with brine (2×50 ml), dried over $MgSO_4$ and evaporated to give a mixture of the 1-methyl and 2-methyl isomers as a gum. Chromatography on silica, eluting with methylene chloride containing 1% (by volume) isopropanol gave two components. The fractions containing the second, more polar component were evaporated to a solid which was recrystallised from ethyl acetate to give the desired product (0.45 g, 34%), m.p. 182°-184° C. Found: C,44.1; H,3.6; N,28.0. $C_{13}H_{13}Cl_2N_7O$ requires C,44.1; H,3.7; N,27.7%. NMR ($CDCl_3$) exhibited a methyl signal at 4.08 consistent with the 1-methyl isomer. m/e 354 (M+).

EXAMPLE 2

2-(2,4-Dichlorophenyl)-1-(1,2,4-triazol-3-yl)-3-(1H-1,2,4-triazol-1-yl)propan-2-ol, dioxalate 3-(2,4-Dichlorophenyl)-3-hydroxy-4-(1H-1,2,4-triazol-1-yl)butyrimidic acid, ethyl ester dihydrochloride (0.5 g) was converted to its free base by partitioning between methylene chloride (20 ml) and saturated sodium bicarbonate solution (5 ml). The organic layer was dried ($MgSO_4$) and evaporated to a gum (0.42 g) under reduced pressure at room temperature. Formyl hydrazine (0.1 g) and ethanol (2 ml) were added and the mixture was stirred at room temperature for 12 hours. The precipitate which formed was collected by filtration and added to toluene (25 ml) containing a trace of para-toluenesulphonic acid. The solution was heated under reflux for 1 hour and the toluene solution was then washed with saturated sodium bicarbonate solution (5 ml), dried over $MgSO_4$ and evaporated to a gum. The product was taken up in a mixture of diethyl ether and ethyl acetate and converted to its oxalate salt by the dropwise addition of a solution of oxalic acid in ethyl acetate. The resulting amorphous solid was collected and dried to yield the title compound (0.108 g, 27%). Hygroscopic. Found: C,37.2; H,3.2; N,15.6. $C_{13}H_{12}Cl_2N_6O.2C_2O_4H_2.H_2O$ requires C,38.0; H,3.5; N,15.6%.

NMR (delta, $CDCl_3$): 3.38(d,J=15 Hz,1H), 3.95(d,J=15 hz,1H), 4.7(d,J=15 Hz,1H), 5.0(d,J=15 Hz,1H), 6.25(bs,1H), 7.05(dd,J=9 Hz,2 Hz,1H), 7.27(d,J=2 Hz,1H), 7.55(d,J=9 Hz,1H), 7.77(s,1H), 7.9(s,1H), 8.15(s,1H).

EXAMPLE 3

2-(2,4-Dichlorophenyl)-1-(1-methyl-1,2,4-triazol-3-yl)-3-(1H-1,2,4-triazol-1-yl)propan-2-ol 2-(2,4-Dichlorophenyl)-1-(2-methyl-1,2,4-triazol-3-yl)-3-(1H-1,2,4-triazol-1-yl)propan-2-ol and 2-(2,4-Dichlorophenyl)-1-(4-methyl-1,2,4-triazol-3-yl)-3-(1H-1,2,4-triazol-1-yl)propan-2-ol The product from Example 2, (0.18 g) as its free base, was stirred with methyl iodide (0.25 g) and potassium carbonate (0.2 g) in acetone (12 ml) at room temperature for 1 hour. The acetone was removed under reduced pressure and the residue taken up in chloroform, filtered and the solution applied to a silica column. Elution with methylene chloride initially containing 2%, rising to 6% isopropanol (by volume) and a trace of ammonia gave three components identified as the three possible N-methyl-triazolyl isomers.

Fraction 1: 45 mg (24%), m.p. 170°-173° C.; m/e 352 (M+)

NMR delta ($CDCl_3$): 3.18(d,J=15 Hz,1H), 3.75(s,3H), 4.0 (d,J=15 Hz,1H), 4.85(s,2H), 6.54(bs,1H), 7.15(dd,J=9 Hz,2 Hz,1H), 7.35(d,J=2 Hz,1H), 7.65(d,J=9 Hz,1H), 7.65 (s,1H), 7.8(s,1H), 8.2(s,1H).

Fraction 2: 44 mg (19%) glass. m/e 270 (M+−82)

NMR delta ($CDCl_3$): 3.14 (d,J=16 Hz,1H), 3.75(s,3H) 3.95 (d,J=16 Hz,1H), 4.85(s,2H), 6.0(bs,1H), 7.05(dd,J=9 Hz, 2 Hz,1H), 7.3(d,J=2 Hz,1H), 7.55(d,J=9 Hz,1H), 7.8(bs,2H), 8.15(s,1H).

Fraction 3: 8 mg (4%) m.p. 190°-193° C. m/e 270 (M+ −82)

NMR delta (CDCl$_3$): 3.27(d,J=16 Hz,1H), 3.55(s,3H), 3.85(d,J=16 Hz,1H), 4.9(s,2H), 6.25(bs,1H), 7.17(dd,J=9 Hz,2 Hz, 1H), 7.37(d,J=2 Hz,1H), 7.7(d,J=9 Hz,1H), 7.8(3,1H), 7.9(s,1H), 8.15(s,1H).

EXAMPLE 4

2-(2,4-Dichlorophenyl)-1-(imidazol-2-yl)-3-(1H-1,2,4-triazol-1-yl)propan-2-ol

A solution of 3-(2,4-dichlorophenyl)-3-hydroxy-4-(1H-1,2,4-triazol-1-yl)butyrimidic acid ethyl ester free base (546 mg), aminoacetaldehyde diethylacetal (234 mg) and acetic acid (210 mg) in tetrahydrofuran (4 ml) was heated under reflux for 2 hours. Hydrochloric acid (4 ml, 5N) was added and the mixture heated to 70° C. for 30 minutes. The mixture was diluted with saturated sodium carbonate to pH8 and extracted with ethyl acetate (3×20 ml). The organic extracts were dried over magnesium sulphate and evaporated to yield a gum which was chromatographed on silica eluting with a mixture of methylene chloride, isopropanol and concentrated ammonium hydroxide (85:15:1 by volume). Fractions containing the desired product were pooled and evaporated to yield a gum which solidified on trituration with diethyl ether (246 mg). Recrystallisation from isopropanol gave the title compound as colourless crystals m.p. 168°-170° C. Found: C,49.8; H,3.9; N,20.9. C$_{14}$H$_{13}$Cl$_2$N$_5$O requires C,49.7; H,3.9; N,20.7%.

EXAMPLE 5

2-(2,4-Dichlorophenyl)-1-(1-methylimidazol-2-yl)-3-(1H-1,2,4-triazol-1-yl)propan-2-ol dimesylate 2-(2,4-Dichlorophenyl)-1-(imidazol-2-yl)-3-(1H-1,2,4-triazol-1-yl)propan-2-ol (80 mg), powdered anhydrous potassium carbonate (200 mg) and methyl iodide (200 mg) were stirred for 3 hours at room temperature in acetone (5 ml). The acetone was evaporated and the residue chromatographed on silica, eluting with a mixture of methylene chloride, isopropanol and concentrated ammonium hydroxide (95:5:1 by volume). Fractions containing the major product were combined and evaporated to a gum which was taken up in ethyl acetate (2 ml) and treated with a solution of methane sulphonic acid in diethyl ether. The precipitate of the dimesylate salt (70 mg) was collected and recrystallised from isopropanol to give the title compound as colourless crystals. m.p. 201°-203° C. Found: C,37.4; N,4.3; N,12.7. C$_{15}$H$_{15}$Cl$_2$N$_5$O.2CH$_3$SO$_3$H requires C,37.5; H,4.2; N,12.9%.

PREPARATION 1

Preparation of 1-cyano-2-(2,4-dichlorophenyl)-3-(1H-1,2,4-triazol-1-yl)propan-2-ol 2-(2,4-Dichlorophenyl)-2-(1H-1,2,4-triazol-1-ylmethyl)oxirane (1.09 g) and sodium cyanide (0.6 g) in dimethylformamide (30 ml) were heated at 65°-70° C. for 1 hour. The reaction mixture was then cooled, poured into water (150 ml), and extracted with ethyl acetate (3×25 ml). The combined organic extracts were washed with saturated aqueous brine, dried (Na$_2$SO$_4$) and evaporated to dryness to give a pale yellow solid (0.76 g) which was triturated with ether. The residual solid was recrystallised from ether/methanol to give the title compound 285 mg (24%), m.p. 217°-219° C. Found: C,48.3; H,3.4; N,18.4. Calculated for C$_{12}$H$_{10}$Cl$_2$N$_4$O: C,48.5; H,3.4; N,18.8%.

PREPARATION 2

Preparation of 3-(2,4-dichlorophenyl)-3-hydroxy-4-(1H-1,2,4-triazol-1-yl)butyrimidic acid, ethyl ester dihydrochloride 1-Cyano-2-(2,4-dichlorophenyl)-3-(1H-1,2,4-triazol-1-yl)propan-2-ol (1 g) was dissolved in dry ethyl alcohol (100 ml) and dry hydrogen chloride gas was bubbled in, at 0° C., for 10 minutes. The reaction mixture was then stirred at room temperature overnight, and then the solvent was decanted from the solid. The solid was then washed with dry ether and dried to yield the title compound, (1.15 g), m.p. 154°-156° C. Found: C,40.6; H,4.4; N,13.6. Calculated for C$_{14}$H$_{16}$Cl$_2$N$_4$O$_2$.2HCl: C,40.4; H,4.4; N,13.5%.

TEST RESULTS

The compounds of the Examples were tested in vivo by oral administration to mice inoculated with a lethal infection of *Candida albicans* according to the procedures described herein. The dose levels providing 50% protection (PD$_{50}$) were as follows:

| Example | PD$_{50}$ (mg/kg/p.o) |
| --- | --- |
| 1 | 0.1 |
| 2 | 2.2 |
| 3 (1) | 1.5 |
| (2) | 20 |
| (3) | 3.5 |
| 4 | 1.2 |
| 5 | 1.0 |

We claim:
1. A compound having the formula

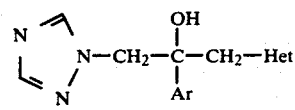

and the pharmaceutically acceptable acid addition salts thereof wherein Ar is dichlorophenyl and Het is selected from the group consisting of 1-methyltetrazol-5-yl, 1,2,4-triazol-3-yl, 1-methyl-1,2,4-triazol-3-yl, 2-methyl-1,2,4-triazol-3-yl, 4-methyl-1,2,4-triazol-3-yl, imidazol-2-yl and 1-methylimidazol-2-yl.

2. A compound of claim 1, wherein Ar is 2,4-dichlorophenyl.

3. The compound of claim 2, wherein Het is 1-methyltetrazol-5-yl.

4. A pharmaceutical composition comprising a compound of claim 1, together with a pharmaceutically acceptable diluent or carrier.

5. A method for treating a human having a fungal infection, which comprises administering to said human an antifungal amount of a compound as claimed in claim 1.

* * * * *